United States Patent [19]
Holt et al.

[11] Patent Number: 5,306,716
[45] Date of Patent: Apr. 26, 1994

[54] METHODS OF ACHIEVING ANTILEUKEMIA ACTIVITY USING 16-MEMBERED-MACROLIDE-TYPE COMPOUNDS

[75] Inventors: Tom G. Holt, Westfield; Richard L. Monaghan, Somerset, both of N.J.

[73] Assignee: Merck & Co., Inc., Rahway, N.J.

[21] Appl. No.: 854,174

[22] Filed: Mar. 20, 1992

[51] Int. Cl.$^5$ .................. A01N 43/02; A61K 31/335
[52] U.S. Cl. .................... 514/185; 514/186; 514/450; 514/460
[58] Field of Search ............ 514/185, 186, 460, 450

[56] References Cited

U.S. PATENT DOCUMENTS

| | | |
|---|---|---|
| 4,385,065 | 5/1983 | Albers-Schoenberg ............ 424/279 |
| 4,390,546 | 6/1983 | Goetz ................................. 424/279 |
| 4,558,139 | 12/1985 | Hagenmaier ...................... 549/271 |

FOREIGN PATENT DOCUMENTS

| | | |
|---|---|---|
| 63-43040 | 2/1988 | Japan . |
| WO91/06296 | 5/1991 | PCT Int'l Appl. . |

OTHER PUBLICATIONS

Wilton et al "PD 118,576: A New Antitumor Macrolide Antibiotic" J. of Antibiotics vol. 28, No. 11, pp. 1449-1452, 1985.

Huang, et al., *Discovery, Production and Purification of the Na+,D+ Activated ATPase Inhibitor, L-681,110* from the Fermentation Broth of Streptomyces SP. MA-5038, Journal of Antibiotics., vol. 37, No. 9, pp. 970-975 (1984).

Goetz, et al., L-155,175: A New Antiparasitic Macrolide Fermentation, Isolation and Structure, Journal of Antibiotics, vol. 38, No. 2, pp. 161-168 (1985).

M. R. Boyd, Status of the NCI Preclinical Antitumor Drug Discovery Screen, Principles and Practices of Oncology, vol. 3, No. 10 (1989).

Hensens, et al., Structure of the Sodium and Potassium Ion Activated Adenosinetriphosphatase Inhbitor L-681,110, J. Am. Chem. Soc., vol 105, pp. 3672-3679 (1983).

Suzukake, et al., Inhibition of Pinocytosis by Hygrolidin Family Antibiotics, J. of Antibiotics, vol. 44, No. 3, pp. 344-348 (Mar. 1991).

U.S. Ser. No. 07/854,167 filed Mar. 20, 1992 to Holt, et al.

*Primary Examiner*—Nathan M. Nutter
*Attorney, Agent, or Firm*—Joseph F. DiPrima; Mark R. Daniel; David A. Muthard

[57] ABSTRACT

Inhibition of renal cancer, melanoma, colon cancer, lung cancer and leukemia cells by administration of compounds from the bafilomycin and hygrolidin groups of compounds.

6 Claims, 4 Drawing Sheets

5,306,716

METHODS OF ACHIEVING ANTILEUKEMIA ACTIVITY USING 16-MEMBERED-MACROLIDE-TYPE COMPOUNDS

FIELD OF THE INVENTION

The invention pertains to the inhibition of certain types of cancerous cells. More specifically, renal cancer, melanoma, lung cancer, colon cancer and leukemia cells are inhibited by administration of compounds from the groups of bafilomycin and hydrolidin and analogs of each of them.

BACKGROUND OF THE INVENTION

Figure 1:
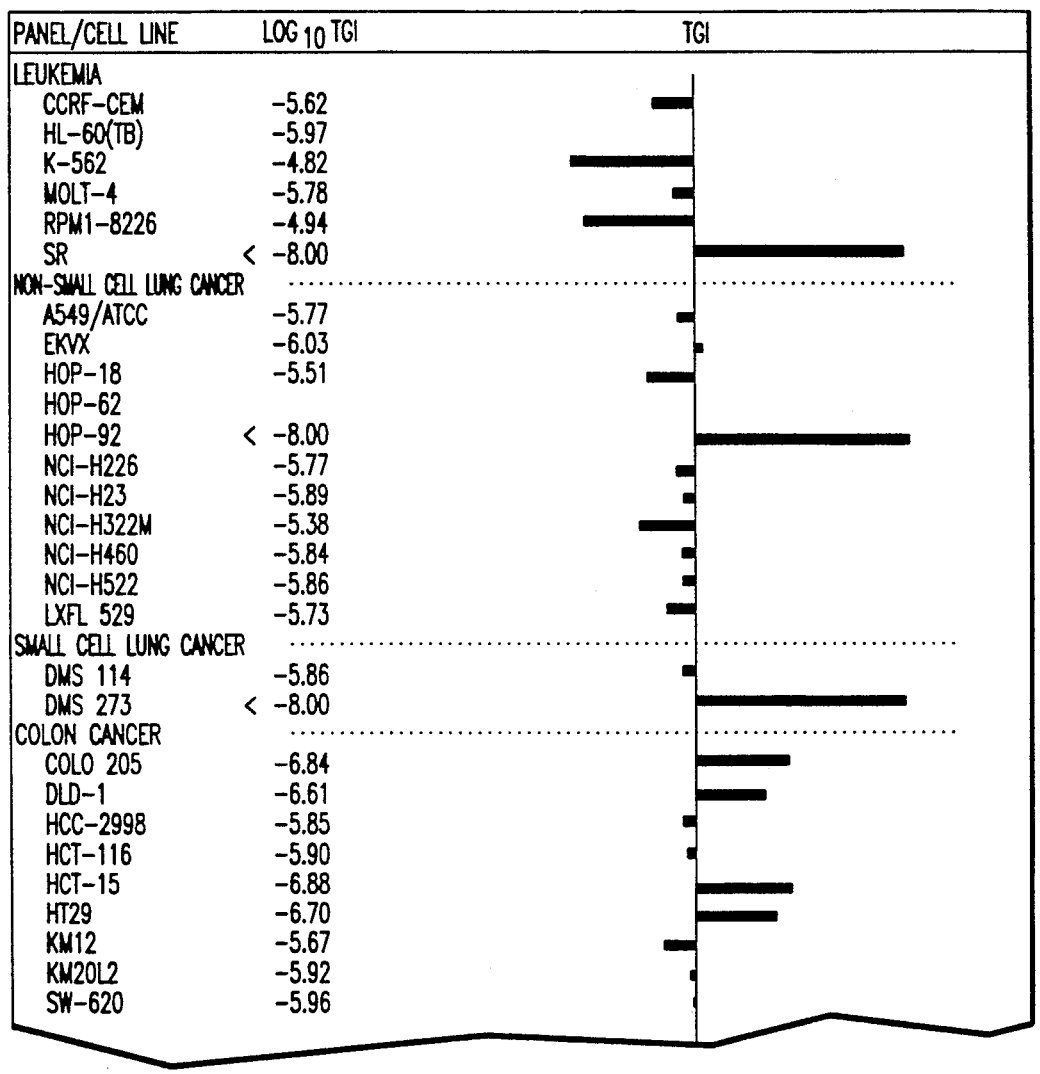
FIG. 1 is a type of bar chart known as a mean graph, showing the Total Growth Inhibition caused by compound number 4 from the table below, upon a panel of some 60 tumor cell lines.
Figure 1:
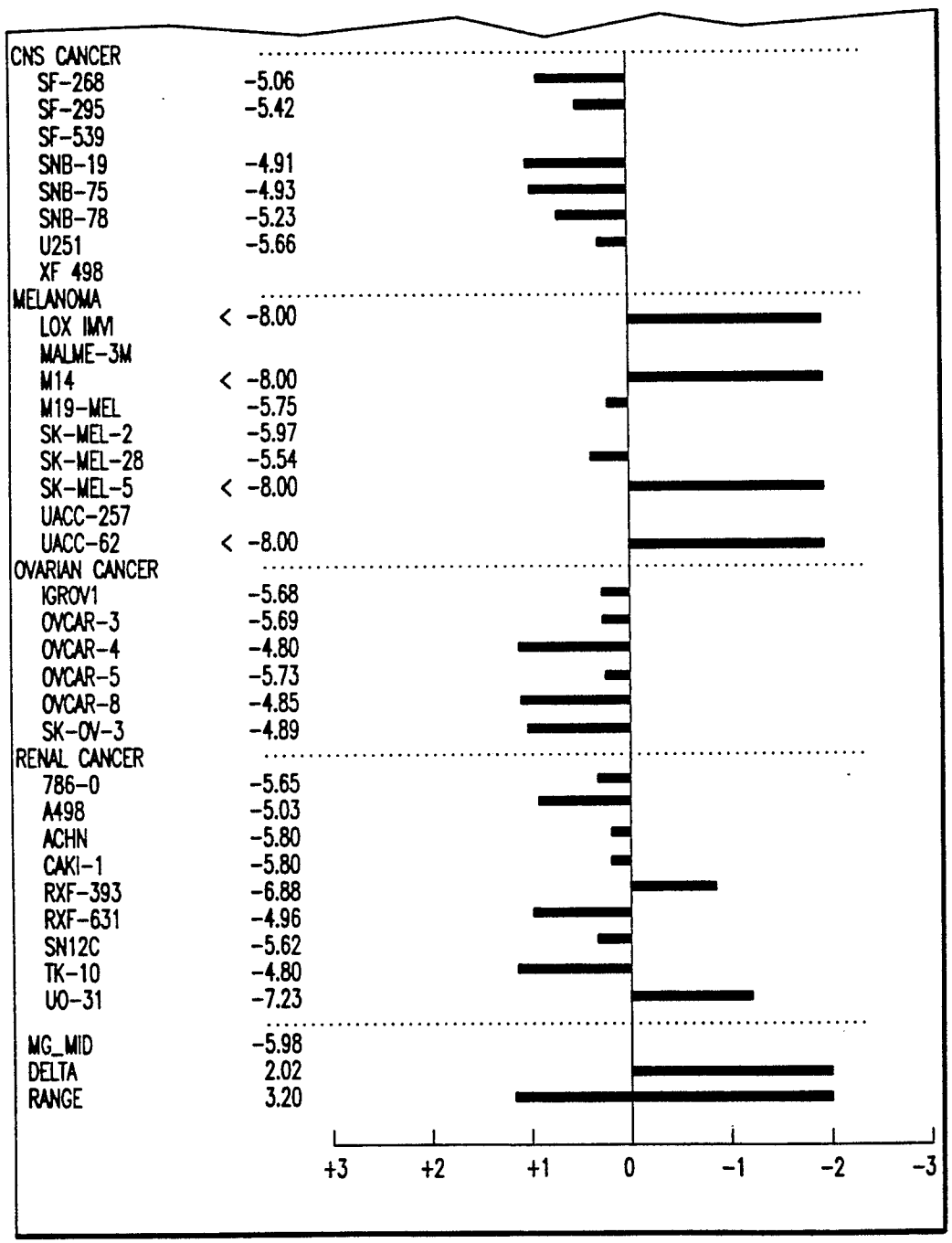

The aforementioned bafilomycins and hygrolidins (which collectively are known as hygrolides) were previously known and shown to have activity as antiparasitics, anthelmintics, antibiotics, insecticides, antifungals, agents for the therapy of bone diseases such as osteoporosis and as $Na^+$, $K^+$ ATP-ase inhibitors leading to increased cardiac function. These compounds share the structural feature of having a 16-membered macrocyclic lactone ring:

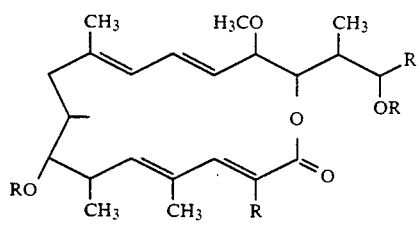

When run through whole tumor-cell assays, compounds from this group have been found to exhibit antitumor activity.

SUMMARY OF THE INVENTION

The invention here is a method of obtaining antitumor activity, in particular against cancers taken from the group consisting of melanoma, renal cancer, lung cancer, colon cancer and leukemia, by administration to mammalian tumor cells of a pharmacologically effective amount of a compound selected from the group consisting of (a) a bafilomycin of the formula

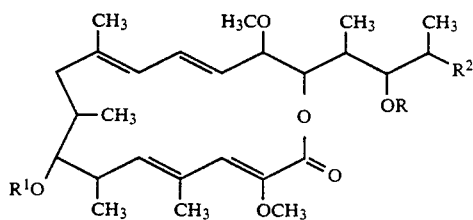

where R is hydrogen or acetyl, $R^1$ is hydrogen or the acyl radical of a carboxylic acid having one to six carbon atoms;

$R^2$ is

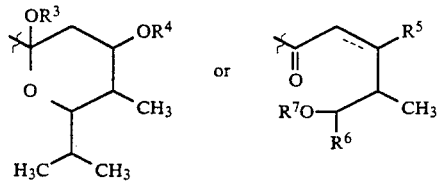

$R^3$ is hydrogen or methyl;

$R^4$ is hydrogen, methyl, the acyl radical of a carboxylic acid having one to six carbon atoms,

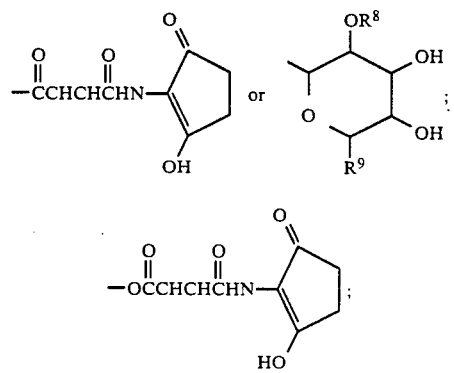

$R^5$ is hydrogen or $R^6$ is methyl or isopropyl;

$R^7$ is hydrogen or acetate;

$R^8$ is hydrogen or methyl;

$R^9$ is hydroxy or methyl; and (b) a hygrolidin of the formula

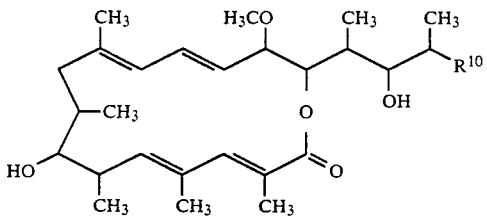

where $R^{10}$ is

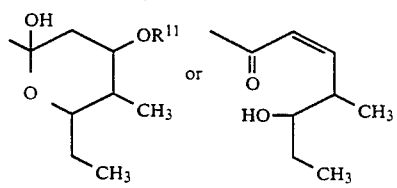

and $R^{11}$ is hydrogen,

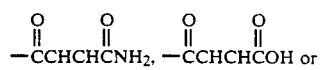

-continued

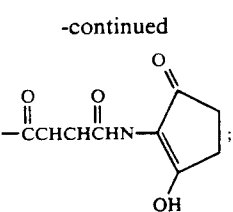

The term "pharmacologically effective amount" shall mean that amount of a drug or pharmaceutical agent that will elicit the biological or medical response of a tissue, system, animal or human that is being sought by a researcher or clinician.

The compounds of the present invention can be administered in such oral dosage forms as tablets, capsules (each including timed release and sustained release formulations), pills, powders, granules, elixirs, tinctures, suspensions, syrups and emulsions. Likewise, they may also be administered in intravenous form (both bolus and infusion), intraperitoneal, subcutaneous or intramuscular form, all using forms well known to those of ordinary skill in the pharmaceutical arts. An effective but non-lethal amount of the compound desired can be employed as an antitumor agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required.

Oral dosages of the present invention, when used for the indicated effects, will range between about 1-25 mg/day orally. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers or hydrogels.

Preferred bafilomycins used in the method of the invention include the following:

| Compound | R¹ | R² |
|---|---|---|
| (1) | H | (structure: tetrahydropyran with OCH₃, OH, CH₃, CH(CH₃)₂ substituents) |
| (2) | H | (structure: tetrahydropyran–OH, ester linkage to fumaramide-N-H to 2-hydroxy-cyclopentenone) |
| (3) | H | (structure: tetrahydropyran with OCH₃, ester linkage to fumaramide-N-H to 2-hydroxy-cyclopentenone) |
| (4) | H | (structure: tetrahydropyran–OH, ester of fumaric acid) |
| (5) | H | (structure: tetrahydropyran with OCH₃, ester of fumaric acid) |
| (6) | H | (structure: tetrahydropyran with OH, OCH₃, CH₃, CH(CH₃)₂) |
| (7) | H | (structure: tetrahydropyran with OH, OC(O)CH₃ acetate, CH₃, CH(CH₃)₂) |

-continued

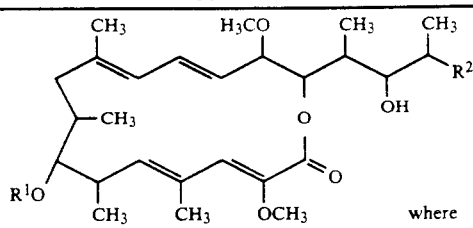

where

| Compound | R¹ | R² |
|---|---|---|
| (8) | −C(=O)CH₃ | [structure: OH, OC(=O)CH₃, O, CH₃, H₃C-CH-CH₃] |
| (9) | H | [structure: OCH₃, OC(=O)CH₃, O, CH₃, H₃C-CH-CH₃] |
| (10) | −C(=O)CH₃ | [structure: OCH₃, OC(=O)CH₃, O, CH₃, H₃C-CH-CH₃] |
| (11) | H | [structure with acyl chain, OH, H₃C-CH-CH₃, amide linked to hydroxycyclopentenone] |

Another group of preferred compounds are set forth as follows:

[macrocyclic structure with R¹O, CH₃, H₃CO, CH₃ CH₃, CH₃, OR³, O, R⁴, OCH₃]

| Compound | R¹ | R³ | R⁴ |
|---|---|---|---|
| (12) | H | H | [CH(OH)CH(CH₃)₂ group] |

[macrocyclic structure with R¹O, CH₃, H₃CO, CH₃ CH₃, CH₃, OR³, O, R⁴, OCH₃]

| Compound | R¹ | R³ | R⁴ |
|---|---|---|---|
| (13) | H | H | [CH(OH)CH(CH₃) group] |
| (14) | −C(=O)CH₃ | −C(=O)CH₃ | [CH(OC(=O)CH₃)CH₃ group] |

Some compounds in the bafilomycin class are sometimes referred to as leucanicidins. Examples include the following:

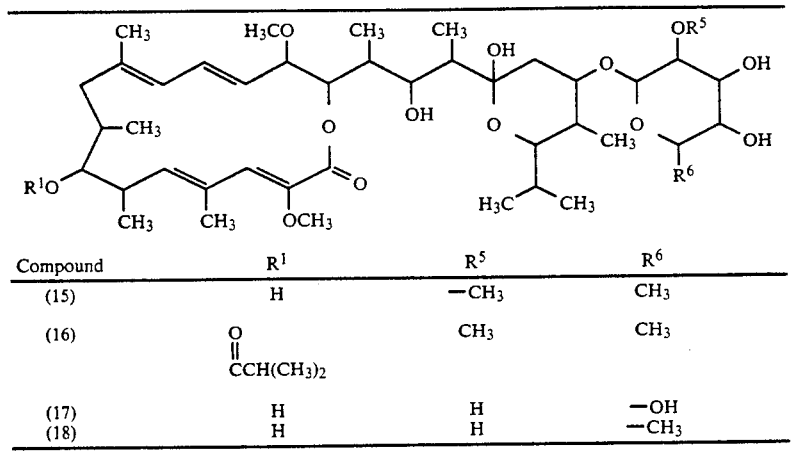

| Compound | R¹ | R⁵ | R⁶ |
|---|---|---|---|
| (15) | H | —CH₃ | CH₃ |
| (16) | O<br>‖<br>CCH(CH₃)₂ | CH₃ | CH₃ |
| (17) | H | H | —OH |
| (18) | H | H | —CH₃ |

Preferred hydrolidins used in the method of the invention include the following

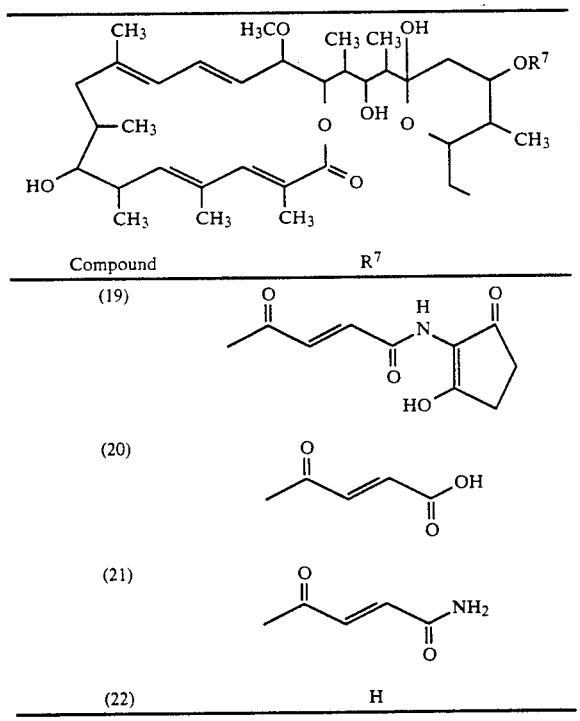

| Compound | R⁷ |
|---|---|
| (19) | (structure) |
| (20) | (structure) |
| (21) | (structure) |
| (22) | H |

An additional preferred compound is oxyhygrolidin:

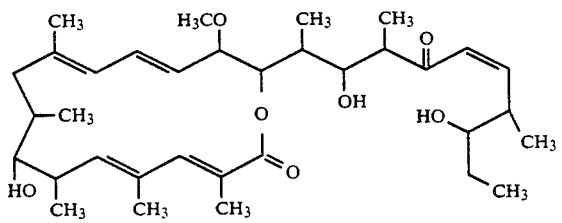

The most preferred compounds of the invention are any or all of those specifically set forth in these examples. These compounds are not, however, to be construed as forming the only genus that is considered as the invention, and any combination of the compounds of their moieties may itself form a genus.

Methods of making bafilomycins are taught in U.S. Pat. Nos. 4,385,065 and 4,558,139 and in Kretschmer et al. Agric. Biol. Chem., 49.8 (1985) 2509-2511. Methods of making leucanicidins are taught in Meyer et al, Helv. Chim. Acta. 68 (1985) 83-94. Methods of making hydgrolidins are taught in U.S. Pat. No. 4,390,546 and in Kretschmer, et al, ibid. The entire disclosure of these patents and journal articles is incorporated herein by reference, and variations of the methods disclosed therein are readily made by those of ordinary skill in the art.

DETAILED DESCRIPTION OF THE INVENTION

An in vitro human tumor drug screen is used to evaluate compounds used in the method of the present invention. The screen employed has been described and the experimental details are taught in the text and bibliography of Boyd, et al., Status of the NCI Preclinical Antitumor Drug Discovery Screen; Principles and Practices of Oncology, Vol. 3, No. 10, October 1989, Lippincott. The screen is a disease-oriented primary screen that employs multiple disease-specific (i.e. tumor-type specific) models. The models are based on the availability of a wide variety of human tumor cell lines, representing many different forms of human cancer. These cell lines comprise a diverse panel of human tumor cell lines arrayed in disease-specific subpanels.

The panel contains a total of 60 human tumor cell lines derived from seven cancer types (lung, colon, melanoma, renal, ovarian, brain and leukemia) that have been adapted to a single growth medium and that have reproducible profiles for growth and drug sensitivity.

EXAMPLE 1

Individual cell lines were initially photographed, expanded (two passages maximum) and cryo-preserved (master stocks) with growth medium and split-ratios recommended by their respective sources. Only cell lines documented to be free of adventitious bacteria and pathogenic viruses (NCI-FCRF[3] Diagnostic Microbiology Lab and Animal Health Diagnostic Lab) were accepted for subsequent characterization. Following recovery of master stocks, cell lines were adapted to a single, standard culture medium: RPMI 1640 (Quality Biologicals, Inc., Gaithersburg, Md.) supplemented with 10% heat-inactivated fetal bovine serum (Sterile Systems Hyclone, Logan, Utah) and 2 mM L-glutamine (NCI-FCRF Central Medium Laboratory) without antibiotics and cultured under conventional culture conditions, that is, 37° C., 5% $CO_2$, 95% air, 100% relative humidity. Cell lines were than expanded (five passages maximum) and cryopreserved for generation of seed stocks. Established adherent cell monolayers approaching 80% confluency were harvested with trypsin/EDTA (NCI-FCRF Central Medium Laboratory) whereas some early passage adherent cell lines were harvested with solution A and 2X-crystalized trypsin III (Sigma Chemical Co.). Leukemia cell lines were subcultured by trituration and dilution. Small cell lung carcinoma cell lines (which generally form large aggregates in suspension under conventional culture conditions) were cultured and assayed in suspension as well as adherent monolayers utilizing poly-L-lysine pretreatment of culture vessels. Following recovery of seed stock, cell lines were subjected to isoenzyme analysis as well as preliminary growth and drug sensitivity assays using one or more in vitro growth inhibition assays (described below). Cell lines meeting basic quality assurance criteria (mycoplasma-negative, MAP-negative, human isoenzymes only) and exhibiting suitable growth profiles were expanded (five serial passages from seed stock, maximum) and cryopreserved as a large number of aliquots designated working seed stock. Cell cryopreservation was achieved using a CryoMed controller (Model 801) and a CryoMed freezing chamber (No. 2700) with a step rate of $-1°$ C./min followed by storage in vapor-phase liquid $N_2$ (NCI-FCRF Central Repository). Cell line seed stocks were tested also for in vivo tumorigenicity (s.c. and i.p. inoculations) in accordance with established protocols. Cell lines recovered from working seed stocks were subjected to repeat mycoplasma tests and to more extensive in vitro growth characterization. Cell lines subsequently were evaluated with respect to stability in drug sensitivity profiles over the course of 20 weekly passages. In addition, each cell line was expanded (eight passages, maximum from seed stock thaw) and cryopreserved as a large number of aliquots ("roller bottle" stock) for in vivo characterization and assay development.

Tetrazolium/formazan reagents were purchased from Sigma Chemical Co. (St. Louis, Mo.): MTT (m2128), MTT formazan (M2003), INT (18377), INT formazan (I7375), and NBT (N6876). DMSO was purchased from Sigma Chemical Co. (D5879), J. T. Baker Chemical Co. (9194-3, Phillipsburg, N.J.), and American Burdick and Jackson Laboratories (Spectrophotometric Grade Product 081, Muskegan, Mich.). These chemicals were stored in unopened bottles at room temperature in the dark or in 50-ml sterile plastic tubes at $-20°$ C. in the dark. Anhydrous isopropanol (505-7) and propylene glycol (P-1009) were purchased from Sigma Chemical Co. Reagent grade hydrochloric acid (A-744) and hexane (H-302-1) were purchased from Fisher Scientific Co. Dimethylformamide (27,054-7) was purchased from Aldrich Chemical Co. (Milwaukee, Wis.) Propanol (spectrophotometric grade 9068-1) was purchased from American Burdick and Jackson Laboratories. Crystalline stock materials were stored at $-20°$ C. Solvent-reconstituted chemotherapeutic agents were prepared at high concentration, partitioned into multiple aliquots, and stored at $-70°$ C. Just prior to culture application the contents of frozen vials were thawed and mixed. Measured aliquots (20–200 $\mu$l) were transferred by micropipet (Gilson Pipetman, Models P200 and P1000) equipped with polypropylene tips to standard culture medium within polypropylene tubes (Sarstedt 62.554/002 or Falcon 2098) and serially diluted in culture medium containing an appropriate concentration of vehicle. In principle, the viable cell number/well is directly proportional to the production of formazan, which following solubilization, can be measured spectrophotometrically. In brief, cells were harvested from exponential-phase maintenance cultures (T-75 $cm^2$ flasks; Falcon Plastics 3023), counted by trypan blue exclusion, and dispensed within replicate 96-well culture plates (Falcon Plastics 3075) in 100-$\mu$l volumes using a repeating pipet (Eppendorf repeater 4780) or multichannel pipet (Flow Labs, Titertek). Following a 24-h incubation at 37° C., 5% $CO_2$, 100% relative humidity (Heraeus $B5060EKO_2$ incubators or NAPCO 5300 incubators), 100 $\mu$l of culture medium, culture medium containing drug or culture medium containing drug vehicle was dispensed within appropriate wells (vehicle control group, $N=6$; each drug treatment group, $N=3$). Peripheral wells of each plate (lacking cells) were utilized for drug blank ($N=2$) and medium/tetrazolium reagent blank ($N=6$) "background" determinations. Culture plates were then incubated for 1 to 11 days prior to the addition of tetrazolium reagent. MTT stock solution was prepared as follows: 5 mg MTT/ml PBS (Quality Biologicals, Inc.) was sterile filtered with 0.45-$\mu$m filter units (Nalgene type SCN) and stored at 4° C. for a maximum of 1 month. MTT working solution was prepared just prior to culture application by diluting MTT stock solution 1:5 (v/v) in prewarmed standard culture medium. Alternatively, other tetrazolium reagents (namely, INT or NBT) were prepared and utilized in a similar fashion for selected experiments. Under standard MTA conditions 50 $\mu$l of MTT working solution was added to each culture well (resulting in 50 $\mu$g MTT/250 $\mu$l to total medium volume) and cultures were incubated at 37° C. for 4 to 24 h depending upon individual cell line requirements. Following incubation cell monolayers and formazan were inspected microscopically: Culture plates containing suspension lines or any detached cells were centrifuged at low speed for 5 min. All but 10–20 $\mu$l of culture medium supernatant was removed from wells by slow aspiration through a blunt 18-gauge needle and replaced with 150 $\mu$l of DMSO (Burdick & Jackson) using a multichannel pipet. Following thorough formazan solubilization (trituration by pipet or vibration on a plate shaker), the absorbance of each well was measured using a microculture plate reader (Dynatech MR600; Alexandria, Va.) at 540 nm (single wavelength, calibration factor=1.00) interfaced with an Apple IIe computer. Subsequently, data were stored and analyzed through use of Apple Soft, Apple Turnover, and Lotus Symphony software. Cell line growth and growth inhibition were expressed in terms of mean ($\pm 1$ SD) absorbance units and/or percentage of control absorbance ($\pm 1$ SD%) following subtraction of mean "background" absorbance. Linearity and reproducibility of instrument measurements were verified by the use of formazan reagents in appropriate solvent systems.

Absorption spectra of formazan reagents as well as cell-generated formazans were measured with a UV/visible scanning spectrophotometer (Perkin-Elmer Lambda V; Perkin-Elmer Corp., Norwalk, Conn.). Samples were placed in 1-cm pathlength disposable polystyrene cuvets (Fisher Scientific Co. 14-385-942) except those solubilized in dimethylformamide solvent which were evaluated in 1-cm pathlength glass spectrophotometer cells (Coleman S7300-4). Freshly prepared material was analyzed in dual beam mode with 2-nm slit width, at 120 nm/min. 0.02 A threshold, and 0.5 s response. Instrument wavelength calibration was verified by examination of deuterium emission spectra to be 653.1±0.3 nm.

Following 1-11 days' incubation, supernatant culture medium was removed and 200 μl of methylene blue (Sigma MB-1) solution [5 g/liter in ethanol:water (50%, v/v)] was added without delay. Following incubation at room temperature for 45 min, unbound stain was removed by plate inversion on absorbant paper and subsequent emersion/dilution in four, 1-liter washes with distilled deionized water. Bound protein stain was solubilized by the addition of 100 μl SDS (Sigma L4509) solution (1%, v/v in water) to each well. Absorbances of wells were measured at 630 nm (single wavelengths, calibration factor=1.00) using equipment and computerized analysis procedures described above for the MTA.

EXAMPLE 2

A more preferred method uses the anionic dye sulforhodamine B (SRB). SRB is a bright pink anionic dye that, in dilute acetic acid, binds electrostatically to the basic amino acids of fixed monolayers of cells. SRB can detect about 1000 cells at 560 nM and 200–300 cells fluorescently. Supermaximal concentration and staining time were determined by dose-response and kinetic analyses. A more preferred medium comprises beta-glycerophosphate as the buffering agent, and the medium has a stable physiological pH of 7.4 in atmospheric $CO_2$. The medium includes biotin, L-asparagine, pyruvate and oxaloacetate for metabolic stimulation of intracellular $CO_2$ production.

EXAMPLE 3

Measures of relative cell line sensitivities are done by comparing relative drug concentrations required to produce the same level of response in each cell line visually. This is presented by a mean graph. Two mean graphs appear at FIGS. 1 and 2. The mean graph, derived from Total Growth Inhibition (TGI) values, is centered at the arithmetic mean of the logarithm of the TGI values for all cell live responses measured for a given compound. The mean graph is construed by projecting bars, one for each cell line (listed by identified on the left of the graph) to either the right or the left of the mean, depending on whether cell sensitivity to the test drug is greater or less than average. The length of a bar is proportional to the difference between the logarithm of the cell line TGI and the mean. For example, for a given cell line, a bar projecting three log units to the right of the mean would reflect an individual cellular sensitivity 1,000 times that of the average of all the cellular responses to the given compound represented on the graph.

Figure 2:
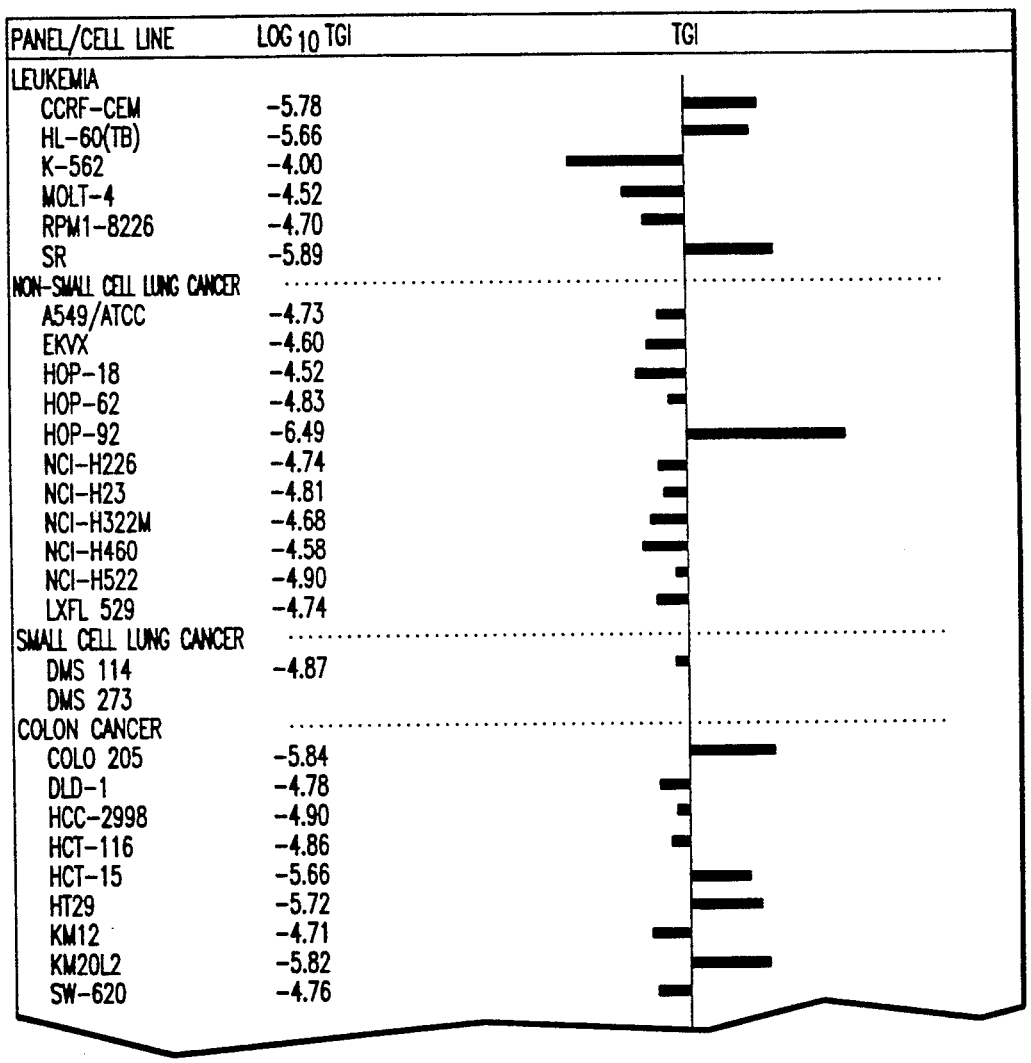
FIG. 2 is the same type of chart as in FIG. 1, showing the Total Growth Inhibition caused by compound number 19 from the table below.
Figure 2:
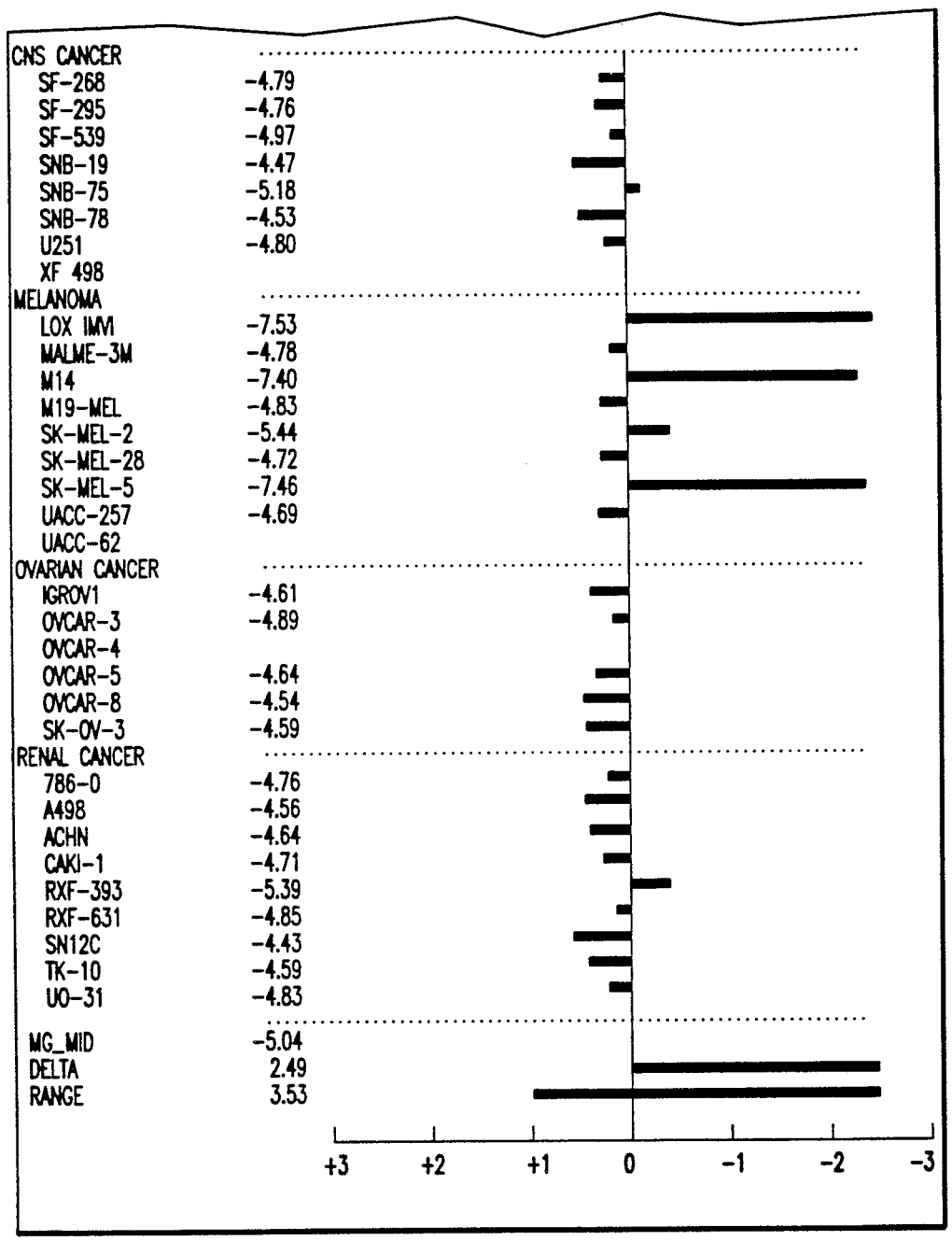

FIGS. 1 and 2 demonstrate that compounds 4 and 19, respectively have especially good antitumor activity against colon cancer cells, renal cancer cells, melanoma cells, lung cancer cells (non-small cells) and leukemia cells. More limited activity is also shown against the other cell lines.

The extrapolation of positive results in the above-described assays to utility as antitumor agents is supported by Boyd, M. R., Status of the NCI Preclinical Antitumor Drug Discovery Screen; Principles and Practices of Oncology, Vol. 3, No. 10, October 1989, Lippincott, the entire disclosure of which is incorporated herein by reference.

What is claimed is:

1. A method of treating leukemia cells in a mammal in need thereof, comprising the step of administering to said mammal a pharmacologically effective amount of a compound selected from the group consisting of a hygrolidin of the formula

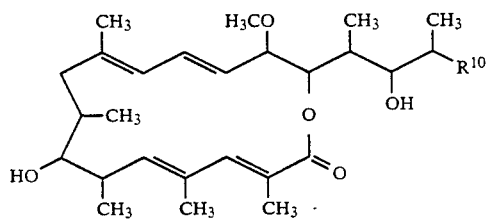

where $R^{10}$ is

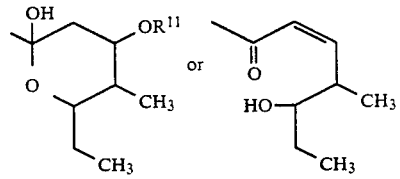

and $R^{11}$ is hydrogen,

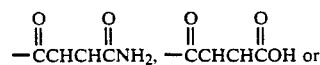

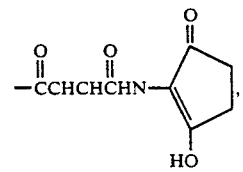

2. The method as claimed in claim 1, wherein said compound administered to said mammal is

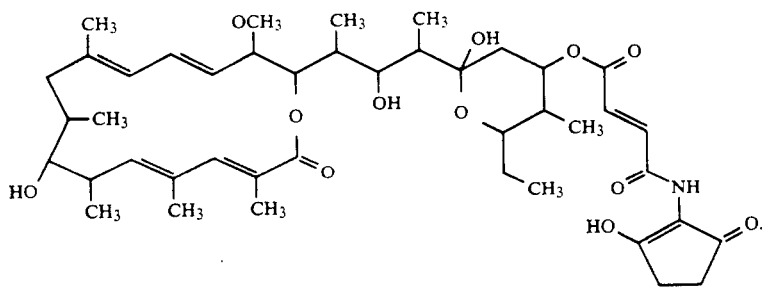
15
3. A method of treating leukemia cells in a mammal in need thereof, comprising the step of administering to said mammal a pharmacologically effective amount of bafilomycin of the formula
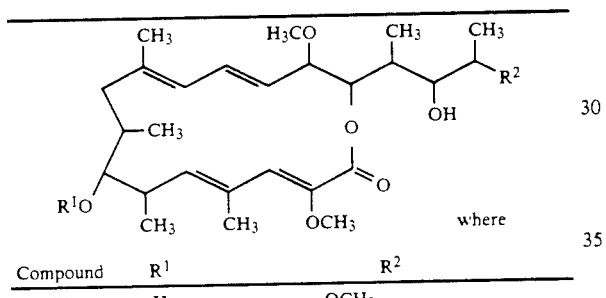
where
| Compound | R$^1$ | R$^2$ |
|---|---|---|
| (1) | H | 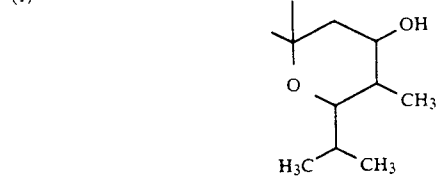 |
| (4) | H | 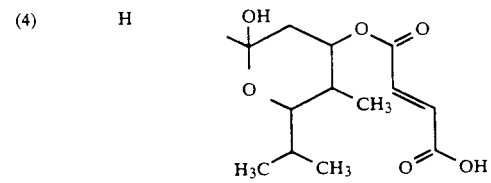 |
| (5) | H | 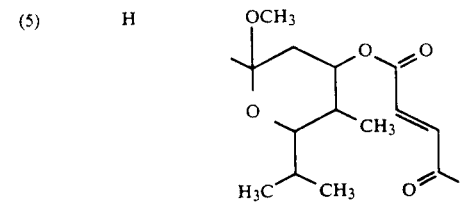 |
| (6) | H | |
-continued
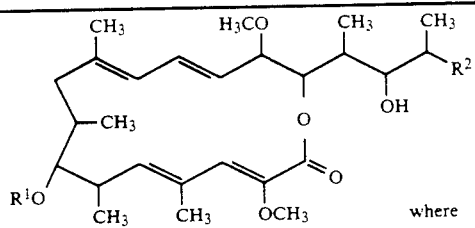
where
| Compound | R$^1$ | R$^2$ |
|---|---|---|
| (7) | H | 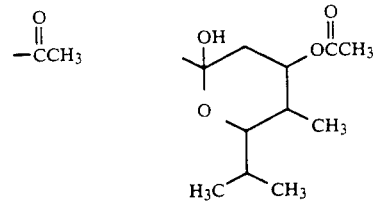 |
| (8) | 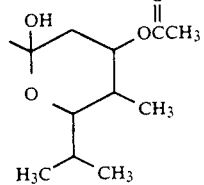 | |
| (9) | H | 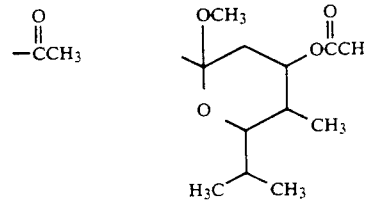 |
| (10) | 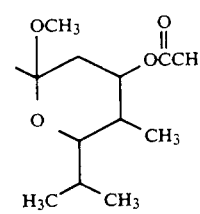 | |

-continued

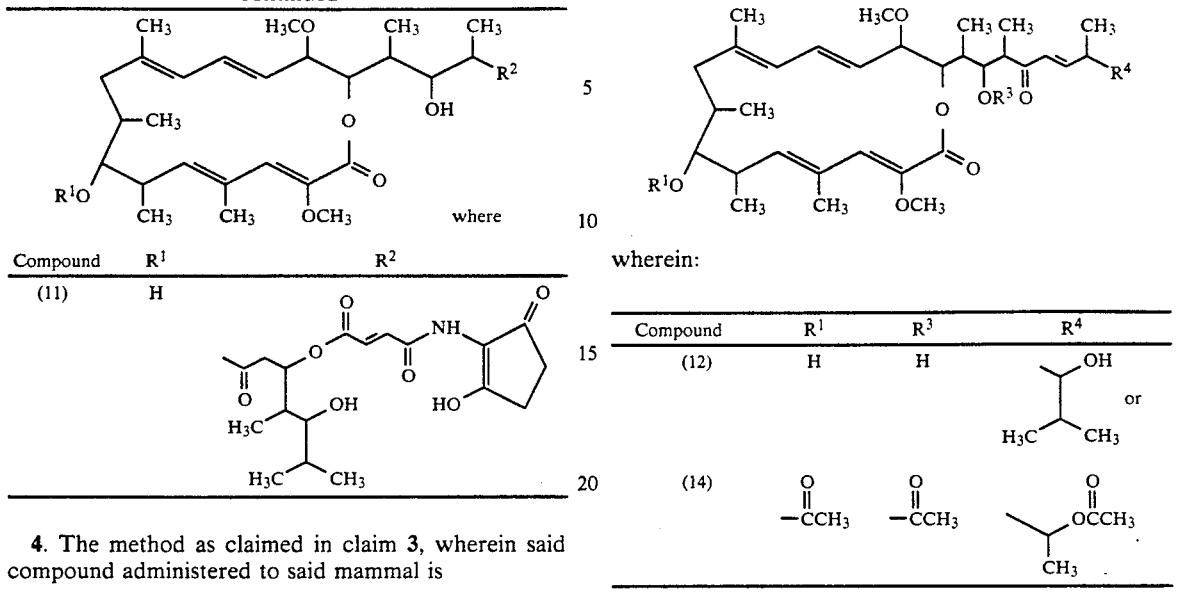

where

| Compound | R¹ | R² |
|---|---|---|
| (11) | H | (structure shown) |

4. The method as claimed in claim 3, wherein said compound administered to said mammal is

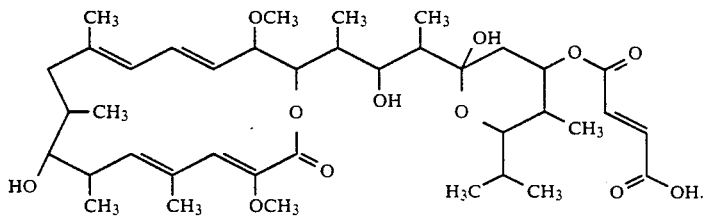

5. A method of treating leukemia cells in a mammal in need thereof, comprising the step of administering to said mammal a pharmacologically effective amount of bafilomycin of the formula wherein:

| Compound | R¹ | R³ | R⁴ |
|---|---|---|---|
| (12) | H | H | $\begin{array}{c}\text{OH} \\ \text{or} \\ H_3C\text{-CH-CH}_3\end{array}$ |
| (14) | $-\overset{O}{\underset{\|}{C}}CH_3$ | $-\overset{O}{\underset{\|}{C}}CH_3$ | $\overset{O}{\underset{\|}{-OCCH_3}}$ with $CH_3$ |

6. A method of treating leukemia cells in a mammal in need thereof, comprising the step of administering to said mammal a pharmacologically effective amount of bafilomycin of the formula

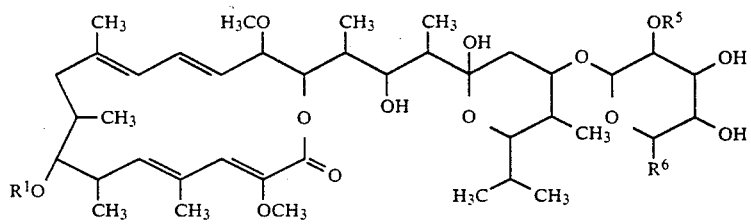

wherein:

| Compound | R¹ | R⁵ | R⁶ |
|---|---|---|---|
| (15) | H | —CH₃ | CH₃ |
| (16) | $\overset{O}{\underset{\|}{CCH(CH_3)_2}}$ | CH₃ | CH₃ |
| (17) | H | H | —OH or |
| (18) | H | H | —CH₃. |

* * * * *